United States Patent [19]

Ikemura et al.

[11] Patent Number: 5,707,611
[45] Date of Patent: Jan. 13, 1998

[54] TOOTH SURFACE TREATING AGENT

[75] Inventors: Kunio Ikemura, Joyo; Yoshiaki Kouro, Hirakata; Hisaaki Tachidokoro, Ibaraki; Katsuya Kimoto, Kawanishi, all of Japan

[73] Assignee: Kabushiki Kaisha Shofu, Kyoto, Japan

[21] Appl. No.: 549,810

[22] PCT Filed: Apr. 6, 1995

[86] PCT No.: PCT/JP95/00665

§ 371 Date: Dec. 7, 1995

§ 102(e) Date: Dec. 7, 1995

[87] PCT Pub. No.: WO95/27470

PCT Pub. Date: Oct. 19, 1995

[30] Foreign Application Priority Data

Apr. 8, 1994 [JP] Japan ................ 6-070914

[51] Int. Cl.$^6$ .............. A61K 7/20; A61K 7/24; A61K 6/02; A61K 6/083
[52] U.S. Cl. .............. 424/53; 424/605; 424/613; 424/57; 424/49; 523/118
[58] Field of Search ............... 523/118; 424/53, 424/49

[56] References Cited

U.S. PATENT DOCUMENTS

| | | |
|---|---|---|
| 4,657,941 | 4/1987 | Hosoda . |
| 4,952,613 | 8/1990 | Blackwell . |
| 5,166,117 | 11/1992 | Imai et al. ................ 502/169 |
| 5,264,513 | 11/1993 | Ikemura . |
| 5,525,648 | 6/1996 | Aasen et al. ................ 523/116 |

FOREIGN PATENT DOCUMENTS

| | | |
|---|---|---|
| 0155812 | 9/1985 | European Pat. Off. . |
| 0335645 | 10/1989 | European Pat. Off. . |
| 0480785 | 4/1992 | European Pat. Off. . |
| 0661034 | 12/1994 | European Pat. Off. . |
| 61-136566 | 6/1986 | Japan . |
| 62-175410 | 8/1987 | Japan . |
| 62-175411 | 8/1987 | Japan . |
| 62-175412 | 8/1987 | Japan . |
| 62-231652 | 10/1987 | Japan . |
| 63-132984 | 6/1988 | Japan . |
| 1279815 | 11/1989 | Japan . |
| 4360808 | 12/1992 | Japan . |
| 51-86309 | 7/1993 | Japan . |
| 2199330 | 6/1988 | United Kingdom . |
| 2261223 | 5/1993 | United Kingdom . |

OTHER PUBLICATIONS

Journal of the Japan Society for Dental Apparatus and Materials, vol. 23, No. 61, pp. 29–33, 1982.

*Primary Examiner*—Peter F. Kulkosky
*Attorney, Agent, or Firm*—Watson Cole Stevens Davis, P.L.L.C.

[57] ABSTRACT

A tooth surface treating agent is provided which comprises a polymerization catalyst and an acidic compound, both water-soluble, the treating agent being capable of enhancing tooth adhesion. The tooth surface treating agent imparts strong adhesion to the enamel and dentin of teeth through simultaneous treatment thereof. The invention is mainly intended for use in the field of dentistry, but is also applicable as a treating agent for vital hard tissues in such fields as surgery, and orthopaedic or plastic surgery.

11 Claims, No Drawings

5,707,611

TOOTH SURFACE TREATING AGENT

This application is a 371 of PCT/JP95/00665, filed Apr. 6, 1995.

INDUSTRIAL UTILIZATION FIELD

The present invention relates to a tooth surface treating agent comprising a polymerization catalyst and an acidic compound which are both soluble in water, the treating agent being capable of enhancing tooth adhesion. More particularly, the invention relates to a tooth surface treating agent for simultaneously treating substrates of vital hard tissues, more particularly enamel and dentin substrates of natural teeth, thereby to impart strong adhesion effect to the substrates.

PRIOR ART

Recently, with the advance of tooth bonding techniques in the field of dentistry, dental restoration through adhesion utilizing a composite resin has been in wide practice. In such situation, a 10–65% phosphoric acid treating agent has been known to be a useful tooth surface treating agent such that it acts to moderately demineralize enamel prisms thereby to impart strong adhesion effect to the enamel through mechanical anchor effect of the resin. Thus, for utilization of such treating agent, clinical techniques are today being established. For use of such agent with dentin, the situation is different. Unlike the case in which the phosphoric acid treating agent is used with the enamel, it has been impracticable to expect that such treating agent can impart strong adhesion effect to the dentin since the pH value of the acid which is very low is apt to cause excessive demineralization of the inorganic component of teeth and softening of the dentin, though some tooth surface cleaning effect is expectable.

More recently, two types of tooth surface treating agents, other than phosphoric acid treating agent, have been used in dental clinics, one comprising 10% citric acid/3% ferric chloride, the other comprising 10% citric acid/20% calcium chloride. Japanese Patent Application Laid-Open No. 5-186309 teaches a tooth surface treating agent which comprises organic acids, such as citric acid, oxalic acid, and maleic acid, iron salt and water, and a tooth surface treating method which comprises use of such treating agent and a bonding material including a barbituric acid derivative. These may be taken as attempts to provide a mordant effect such that the dentin softened by acid treatment is reinforced by metallic chloride. In reality, however, where a collagen layer is formed as a result of demineralization of inorganic component, or where post-treatment water washing of the tooth surface is insufficient, some calcium salt of undissolved acid may deposit on the tooth surface, which prevents the provision of any strong bond effect. According to the experiments conducted by the present inventors, the use of these tooth surface treating agents failed to provide any sufficient bond strength.

In this way, various types of tooth surface treating agents have hitherto been used Which comprise phosphoric acid, citric acid, maleic acid, oxalic acid and/or a combination of any such acid and a metallic chloride, but what can be expected of such treating agent is limited to the demineralization of inorganic component and tooth surface cleaning effect. As such, with these treating agents, it has been impracticable to impart strong adhesion effect to the substrates of enamel and dentin. Therefore, from a standpoint of dental clinics, there has been a strong need for an improved tooth surface treating agent which contributes to clinical operation simplicity such that the treating agent can simultaneously treat both the enamel and the dentin and impart strong adhesion effect to them.

SUBJECT THAT THE INVENTION IS TO SOLVE

The present invention has been made in view of the foregoing situation and, accordingly, it is an object of the invention to provide a tooth surface treating agent which can be advantageously used for simultaneous treatment of the enamel and dentin substrates of natural teeth thereby to impart strong adhesion effect to them.

MEANS OF SOLVING THE SUBJECT

The invention relates a-tooth surface treating agent comprising a polymerization catalyst and an acidic compound, both water-soluble, the treating agent being capable of enhancing tooth adhesion.

In their pursuit of a tooth surface treating agent for use with dental resin for dentin adhesion which has, in addition to its role to demineralize the inorganic ingredients of acidic compounds and clean the surface of teeth, a function to increase the polymerization rate of the resin at an adhesive interface for the polymerization catalyst, the present inventors discovered that a tooth surface treating agent comprising a polymerization catalyst and an acidic compound, both water-soluble, which is capable of enhancing teeth adhesion would impart strong adhesion property to the enamel and dentin substrates of natural teeth through simultaneous treatment thereof.

Polymerization catalysts useful in the present invention are radical polymerization catalysts for which may be mentioned initiators and accelerators for chemical polymerization catalysts and initiators and accelerators for photopolymerization catalysts. In particular, ascorbic acids, barbituric acid derivatives, organic peroxides, sulfinic acids, and photopolymerization catalysts are preferably used.

Ascorbic acids may be exemplified by L-ascorbic acid derivatives and more preferably by L-ascorbic acid. L-ascorbic acid, generally known as vitamin C, is used in the prevention and cure of scurvy, and it is widely known that L-ascorbic acid is a highly safe substance to a living body and serves as good in vivo activator. Thus, it is expectable that L-ascorbic acid can have mild effect upon the dentin and pulp. Further, with their attention paid to the fact that L-ascorbic acid is an acidic polymerization catalyst, the present inventors developed another aspect of the present invention in which the tooth surface treating agent comprises the polymerization catalyst, the acidic compound and water, finding that the tooth surface treating agent would impart strong adhesion property to the enamel and dentin of teeth. Therefore, the tooth surface treating agent of the invention which includes L-ascorbic acid is especially preferred in the sense that it has three roles, namely, provision of in vivo activation effect, demineralization of inorganic ingredients, and improved rate of resin polymerization.

Barbituric acid derivatives are expressed by the following general formula (1):

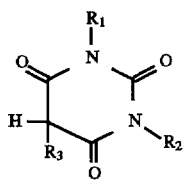

(1)

(where, $R_1$, $R_2$, and $R_3$ may be same or different and each may represent an aliphatic, aromatic, alicyclic, or heterocyclic residue or hydrogen atom which may have a substituent, such as halogen atom, alkyl group, alkoxy group, aryl group, or cyclohexyl group.) To give specific examples, the following may be enumerated: barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-n-butylbarbituric acid, 1,3-dimethyl-5-isobutylbarbituric acid, 1,3-dimethyl-5-tert-butylbarbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-5-ethylbarbituric acid, 1-benzyl-5-phenylbarbituric acid, and thiobarbituric acids; and salts of these (in particular, alkali metals and alkali earth metals are preferred), for example, sodium 5-butylbarbiturate, sodium 1,3,5-trimethylbarbiturate, and sodium 1-cyclohexyl-5-ethylbarbiturate. Barbituric acid derivatives which are particularly preferred are: 5-butylbarbituric acid, 1,3,5-trimethylbarbituric acid, 1-cyclohexyl-5-ethylbarbituric acid, and 1-benzyl-5-phenyl barbituric acid. These barbituric acid derivatives react with any of those acidic compounds which contain a metallic chloride or a halogen group. Also, of the barbituric acid derivatives, metal salt of barbituric acid reacts with acidic compounds. Therefore, where any such reactable barbituric acid derivative and any such reactable acidic compound are to be used in combination, it may be arranged that the barbituric acid derivative and the acidic compound are separately prepared without being mixed together and that solutions of the respective ingredients are mixed immediately before they are applied for tooth surface treatment. Alternatively, one of the two solutions is applied directly to the tooth surface, the other being then applied over the one solution first applied. In either of these ways, the present invention can be successfully carried into practice.

Organic peroxides available for use in the invention include, for example, benzoylperoxide, 2,4-dichlorobenzoylperoxide, isobutylperoxide, t-butyl hydroperoxide, succinic acid peroxide, t-butylperoxy maleic acid, t-butylperoxyisobutylate, t-butyl perbenzoate, and stearylperoxide. Particularly preferred of these are t-butyl hydroperoxide, succinic acid peroxide, and t-butylperoxy maleic acid, which are water-soluble and have an acid radical.

Sulfinic acids useful for the purpose of the invention include sulfinic acid, alkali metal salt of sulfinic acid, and sulfinamides. More specifically, sulfinic acids include, for example, benzenesulfinic acid, p-toluenesulfinic acid, dodecylbenzenesulfinic acid, benzenesulfinic acid sodium salt, p-toluenesulfinic acid sodium salt, dodecylbenzenesulfinic acid sodium salt, benzenesulfinamide, p-toluenesulfinamide, N,N-dimethyl-p-toluenesulfinamide, benzenesulfinic acid morpholide, and p-toluenesulfinic acid morpholide. Of these sulfinic acids, especially preferred are benzenesulfinic acid sodium salt and p-toluenesulfinic acid sodium salt. Metallic salts of these sulfinic acids react with acidic compounds. Therefore, where any such metallic salt is to be used in combination with the acidic compound, it may be arranged that a solution of the sulfinic acid metal salt and a solution of the acidic compound are separately prepared without being mixed together and that solutions of the respective ingredients are mixed immediately before they are applied for tooth surface treatment. Alternatively, one of the two solutions is applied directly to the tooth surface, the other being then applied over the one solution first applied. In either of these ways, the present invention can be successfully carried into practice.

Examples of photopolymerization catalysts include benzoin methyl ether, benzoin isopropyl ether, 2-chlorothioxanthone, camphorquinone, benzyl, diacetyl, 2-hydroxy-3-(3,4-dimethyl-9H-thioxanthene-2-iroxy)-N,N,N-trimethyl-1-propane ammonium chloride, N,N-dimethyl aminoethylmethacrylate, N,N-diethylaminomethacrylate, N-phenylglycine, di-n-butyl-tin-maleate, d-n-butyl-tin-dilaurate, and dioctyl-tin-dilaurate. Of these, camphorquinone is particularly preferred.

These polymerization catalysts may be used alone, or in combination with two or more kinds of compounds selected from any of the foregoing groups of ascorbic acids, barbituric acid derivatives, organic peroxides, sulfinic acids, and photopolymerization catalysts. Alternatively, two or more kinds of compounds may be used in combination so as to provide a mixture of compounds selected from the foregoing groups of ascorbic acids, barbituric acid derivatives, organic peroxides, sulfinic acids, and photopolymerization catalysts.

The proportion of the polymerization catalyst used in the invention is preferably 0.01 to 30% by weight, more preferably 0.1 to 25% by weight. If the proportion is less than 0.01% by weight or more than 30% by weight, the resulting adhesion effect will be unsatisfactory.

Acidic compounds useful for the purpose of the invention are compounds which exhibit acidity when they are dissolved in water. More particularly, the term "acidic compound" herein refers to a compound which contains more than one of phosphoric acid group, carboxyl group, acid anhydride residue, hydroxyl group, cyclic acid group, or halogen group; or a monomer, oligomer, or polymer which contains an acidic group; or an inorganic acid or metallic chloride.

Examples of acidic compounds include phosphoric acid, citric acid, acetic acid, propionic acid, butyric acid, valeric acid, caproic acid, caprylic acid, capric acid, lauric acid, myristic acid, palmitic acid, stearic acid, cyclohexane carboxylate, cinnamic acid, phenylacetic acid, thioctic acid, benzoic acid, o-, m-, p-toluic acid, o-, m-, p-chlorobenzoic acid, o-, m-, p-bromobenzoic acid, o-, m-, p-nitrobenzoic acid, phthalic acid, salicylic acid, p-hydroxybenzoic acid, anthranilic acid, o-, m-, p-aminobenzoic acid, o-, m-, p-methoxy benzoic acid, p-amino salicylic acid, 4-amino-n-butyric acid, 5-amino valeric acid, trimellitic acid, oxalic acid, malonic acid, succinic acid, glutaric acid, adipic acid, pimelic acid, suberic acid, sebacic acid, 1,10-decanedicarboxylic acid, tartaric acid, maleic acid, fumaric acid, malic acid, nitric acid, hydrochloric acid, iron (II) chloride, ferric chloride, cuprous chloride, cupric chloride, and stannous chloride. Additionally, as examples of polymerizable monomers, oligomers, and polymers which contain acidic group, the following may be enumerated: 4-(meth)acryloxyethyltrimellitic acid [which means 4-methacryloxyethyltrimellitic acid and/or 4-acryloxyethyltrimellitic acid; the same will apply mutatis mutandis hereinafter], 4-(meth)acryloxyethyltrimellitic acid anhydride, 11-(meth)acryloxy-1,1-undecane dicarboxylic acid, bis[2-(meth)acryloxyethyl] phosphoric acid, (2-(meth) acryloxy ethyl phenyl) phosphoric acid, p-vinyl phosphonic acid, p-vinylbenzyl phosphonic acid, N-(meth) acryloylamino salicylic acid; polyacrylic acid, polyitaconic acid, and polymaleic acid, or copolymers of these; and polyalkene acids having an unsaturated group on their side chains. Especially preferred acidic compounds are phosphoric acid, tartaric acid, maleic acid, citric acid, ferric chloride, 4-acryloxyethyltrimellitic acid, 4-acryloxyethyltrimellitic acid anhydride, and polyacrylic acid. These acidic compounds may be used alone or in combination of two or more kinds.

The proportion of the acidic compound(s) is from 1 to 70% by weight, preferably from 3 to 35% by weight. If the proportion is less than 1% by weight or more than 70% by weight, the resulting adhesion effect will be unsatisfactory.

A mixture of such polymerization catalyst and such acidic compound, as one form of tooth surface treating agent of the invention, may, after a cavity is prepared on a tooth surface, followed by water washing, be applied directly to the wet tooth surface. The polymerization catalyst and the acidic compound may be used in mixture with a predetermined amount of water.

The water to be used in the present invention is preferably such that it has good storage stability, meets clinically accepted standards for medical-use ingredients, and does not essentially contain any impurities harmful to the ingredients and adhesion aspect of the composition. For this purpose, distilled water (or purified water) or ion-exchanged water (deionized water) is preferably used.

The proportion of water in the tooth-surface treating agent is 100 wt % less a total proportion of the polymerization catalyst and acidic compound, preferably 10 to 98 wt %. If the proportion is less than 10% by weight, the dissolution of the polymerization catalyst and acidic compound is considerably hindered. If the proportion is more than 98% by weight, the resulting adhesion effect is unfavorable.

In the present invention, a solvent may be used in mixture with the principal ingredients. Solvents to be used are not particularly limited only if they can facilitate the dissolution of the polymerization catalyst and acidic compound. For this purpose, ethyl alcohol, isopropyl alcohol, and acetone are preferably used. These solvents may be used alone or in a combination of two or more kinds. Solvents may be used in mixture with water. A solvent having a boiling point lower than water is useful for facilitating the process of water washing and drying after tooth surface treatment. The proportion of the solvent is 100 wt % less a total proportion of the polymerization catalyst and acidic compound, and is preferably within the range of from 10 to 98% by weight.

In the present invention, oxidation inhibitors, such as hydroquinone, hydroquinone monomethyl ether, and butylated hydroxytoluene, may be suitably used. Also, viscosity modifiers, such as colloidal silica, glycerin, and polyethylene glycol, may be used in gel form.

The proportion of the oxidation inhibitor is preferably from 0.01 to 10 % by weight, and the proportion of the viscosity modifier is preferably from 0.5 to 20 % by weight.

In use, the tooth surface treating agent may be applied in such a manner that, after a cavity is prepared in the teeth, the mixture of the polymerization catalyst and acidic compound is directly applied to the wet tooth surface. As an alternative, the polymerization catalyst, acidic compound, and water can be previously mixed in predetermined proportions and the mixture is used as tooth surface treating agent. As another alternative, the mixture of the polymerization catalyst, acidic compound, and water may be mixed with desired additives in predetermined proportions, the resulting mixture being used as tooth surface treating agent. The tooth surface treating agent may be divided into two or more parts for use. Before application to the dentin and enamel surfaces of teeth of any such dental material as primer, bonding agent, composite resin, resin cement, fissure sealant, or orthodontic adhesive, the tooth surface treating agent is applied to such surface in a proper amount, and the surface to which the treating agent is so applied is then washed with water and dried or simply dried.

The tooth surface treating agent of the present invention can be applied as such in conjunction with various other dental materials which are commercially available today, including dental cements, such as glassionomer cement, photopolymerization type glassionomer cement, and poly (meth)acrylate-based resin cement. The composition of the invention can be also used as a treating agent for bond surfaces with respect to metallic crowns and inlay.

The invention is mainly intended for use in the field of dentistry, but is also applicable as a treating agent for vital hard tissues in such fields as surgery, and orthopaedic or plastic surgery.

EXAMPLES

The following examples are given to further illustrate the present invention. It is understood, however, that the invention is not limited by these examples.

Examples 1–6 and Comparative Examples 1–3

Using tooth surface treating agents prepared in mix proportions of L-ascorbic acid, ferric chloride, and distilled water as shown in Table 1 below, shear bond tests were carried out with respect to tooth surfaces.

The "Imperva Bond" dentin primer (Shofu Inc.) was used as primer, and "Imperva Bond" bonding agent (Shofu Inc.) was used as light-cure type bonding agent. Also, "LITE-FIL II" (Shofu Inc.) was used as light-cure type composite resin.

Bond strength was determined by the shear bond strength of the composite resin in relation to the enamel and dentin. Freshly extracted bovine anterior teeth were used instead of human teeth, with cutting off the root portions being embedded in an epoxy resin mass applied therearound.

For purposes of bond tests, the labial surface of the bovine teeth was subjected to sanding with a water-resistant sandpaper, whereby the enamel and dentin were exposed. After #600 grinding, treatment was effected with each respective tooth surface treating agent in Table 1 for 30 seconds, followed by water washing and drying. Thereafter, "Imperva Bond" dentin primer was applied with a small brush and, 30 seconds later, compressed air drying was effected. Then, a double-faced tape with a perforation of 4 mm dia. was applied to the surface to specify the bond surface, and "Imperva Bond" bonding agent was applied to the specified surface, which in turn was subjected to visible light irradiation by "Shofu" GRIP LIGHT II (Shofu Inc.) for 30 seconds, so that the surface was photo-cured. Subsequently, a plastic mold with an inner diameter of 4 mm and a height of 2 mm was fixed to the surface and "LIGHT-FIL II" was filled into the interior of the mold. The surface was subjected to visible light irradiation by "Shofu" GRIP LIGHT II via the mold for 30 seconds. After light curing, the mold was removed and a bond test specimen was prepared for each tooth surface treating agent.

The bond test specimen was immersed in distilled water at 37° C. for 24 hours. Then, measurement for shear bond strength was made by "Shimadzu" AUTOGRAPH AG-5000G at a crosshead speed of 1 mm/min.

For purposes of comparison, bond tests were also conducted for the case where the ingredients were L-ascorbic acid and water only; the case where the ingredients were ferric chloride and water only; and the case where any tooth surface treating agent was not used. The results are shown in Table 1.

TABLE 1

| Ingredient & bond strength | Ex. 1 | Ex. 2 | Ex. 3 | Ex. 4 | Ex. 5 | Ex. 6 | Comp. Ex. 1 | Comp. Ex. 2 | Comp. Ex. 3 |
| --- | --- | --- | --- | --- | --- | --- | --- | --- | --- |
| L-ascorbic acid | 5 | 10 | 15 | 15 | 20 | 25 | 10 | — | — |
| Ferric chloride | 3 | 3 | 2 | 10 | 1 | 1 | — | 3 | — |
| Distilled water | 92 | 87 | 83 | 75 | 79 | 74 | 90 | 97 | — |
| Bond strength (kgf/cm$^2$) | | | | | | | | | |
| for enamel | 160.8 | 155.7 | 186.9 | 214.5 | 150.1 | 166.2 | 102.7 | 74.0 | 72.0 |
| for dentin | 134.8 | 206.0 | 167.4 | 150.4 | 155.2 | 188.7 | 70.5 | 39.5 | 125.4 |

(Note) Ingredient proportions are shown in wt %.

From the above results, it is apparent that the tooth surface treating agents, or the compositions of L-ascorbic acid/ferric chloride/water, can impart high bond effect to the enamel and dentin through simultaneous treatment thereof. No such effect was observed with Comparative Examples 1–3.

Example 7 and Comparative Examples 4 and 5

A tooth surface treating agent was prepared in the mixing proportions of L-ascorbic acid, citric acid, calcium chloride, ferric chloride, and distilled water as shown in Table 2. Shear bond tests with bovine teeth were carried out in the same way as in Example 1, except that the following primers were used with the tooth surface treating agent shown in Table 2.

A composition prepared from a mixture of 30 parts by weight of distilled water, 30 parts by weight of 2-hydroxyethyl methacrylate, 40 parts by weight of 4-acryloxyethyltrimellitic acid, 3 parts by weight of triethyleneglycoldimethacrylate, 0.6 part by weight of camphorquinone, and 0.8 part by weight of N,N-dimethylaminoethylmethacrylate was used as a primer. For the light curing bonding agent and light-cure composite resin, the same ones as those used in Example 1 were employed.

For purposes of comparison, bond tests were also carried out for conventional tooth surface treating agents of 10% citric acid/3% ferric chloride and of 10% citric acid/20% calcium chloride. Further, pH measurements were made using a pH meter with respect to respective tooth surface treating agents. The results are shown in Table 2.

TABLE 2

| Ingredient & bond strength | Example 7 | Comparative Example 4 | Comparative Example 5 |
| --- | --- | --- | --- |
| L-ascorbic acid | 10 | — | — |
| Citric acid | — | 10 | 10 |
| Calcium chloride | — | 20 | — |
| Ferric chloride | 3 | — | 3 |
| Distilled water | 87 | 70 | 87 |
| Bond strength to enamel (kgf/cm$^2$) | 207.4 | 193.2 | 170.9 |
| Bond strength to dentin (kgf/cm$^2$) | 169.3 | 89.7 | 89.2 |
| pH value | 1.05 | 0.66 | 0.14 |

(Note) Ingredient proportions are shown in wt %.

As is apparent from Table 2 results, the composition of the invention in Example 7 was comparatively high in pH value and exhibited high bond effect in relation to the enamel and dentin. In particular, the composition exhibited significantly high bonding effect with the dentin as compared with those in comparative examples. In Comparative Examples 4 and 5, which represent the prior art, high bonding effect with the enamel was observed, but the bond with the dentin was low. The results indicate that the conventional compositions are unsuitable for use as tooth surface treating agents for simultaneous treatment of the enamel and dentin.

Examples 8 to 11 and Comparative Examples 6 and 7

Tooth surface treating agents were prepared in varying mixing proportions of 1,3,5-trimethylbarbituric acid (TMBA), phosphoric acid, tartaric acid, and distilled water as shown in Table 3. Shear bond tests with bovine teeth were carried out in the same way as in Example 1, except that tooth surface treating agents shown in Table 3 were used and that the time for tooth surface treatment and the time for primer treatment were both set at 15 seconds.

For purposes of comparison, bond tests were similarly carried out with two kinds of tooth surface treating agent, one being composed of 1,3,5-trimethylbarbituric acid only except distilled water, the other being composed of tartaric acid only except distilled water. The results are shown in Table 3.

TABLE 3

| Ingredient & bond strength | Example 8 | Example 9 | Example 10 | Example 11 | Comparative Example 6 | Comparative Example 7 |
|---|---|---|---|---|---|---|
| TMBA | 3 | 3 | 3 | 1 | 3 | — |
| Phosphoric acid | 10 | 3 | — | — | — | — |
| Tartaric acid | — | — | 10 | 40 | — | 10 |
| Distilled water | 87 | 94 | 87 | 59 | 97 | 90 |
| Bond strength (kgf/cm$^2$) | | | | | | |
| to enamel | 191.7 | 254.7 | 167.5 | 198.9 | 86.8 | 128.4 |
| to dentin | 173.1 | 271.6 | 168.8 | 139.5 | 122.6 | 84.4 |

(Note) Ingredient proportions are shown in wt %.

From Table 3 results, it is apparent that tooth surface treating agents which are composed of polymerization catalyst, acidic compound, and water as in Examples 8 to 11 can impart high bond effect to both the enamel and the dentin. The results indicate that they are effective for use as tooth surface treating agents for simultaneous treatment of the enamel and dentin. In contrast, compositions of Comparative Examples 6 and 7, wherein either polymerization catalyst or acidic compound was not present, could not provide any sufficient adhesion with respect to the adherends and were found unsatisfactory for tooth surface treating purposes.

Examples 12 to 15 and Comparative Example 8

Using tooth surface treating agents prepared in mix proportions of phosphoric acid, 1,3,5-trimethylbarbituric acid (TMBA), and distilled water as shown in Table 4 below, tensile bond tests were carried out with respect to freshly extracted bovine anterior teeth.

A composition prepared from a mixture of 47 parts by weight of di(methacryloxyethyl)trimethylhexamethylene diurethane, 14 parts by weight of triethyleneglycoldimethacrylate, 35 parts by weight of 2-hydroxyethyl methacrylate, 3 parts by weight of 4-acryloxyethyltrimellitic acid, 1 part by weight of 4-acryloxyethyltrimellitic acid anhydride, 0–8 part by weight of camphorquinone, and 1.0 part by weight of di-n-butyl tin laurate was used as light-cure bonding agent. For the primer and light cure composite resin, those used in Example 1 were employed.

For purposes of bond tests, bovine anterior teeth having dental pulp, as extracted at a lower jaw portion immediately after morning slaughter, was used in their with pulp condition (which teeth may be hereinafter referred to as freshly extracted bovine teeth with pulp). Bond tests were carried out within 10 hours after teeth extraction (pulp cells are alive 30 hours or so after extraction). The labial surface of the bovine teeth was subjected under water pouring to sanding with a water-resistant sandpaper, whereby the dentin surface was exposed. After #600 smooth sanding, treatment was effected with each respective tooth surface treating agent in Table 4 for 15 seconds, followed by water washing and drying. Thereafter, "Imperva Bond" dentin primer was applied with a small brush and, 15 seconds later, compressed air drying was effected. Then, a double-faced tape with a perforation of 4 mm dia. was applied to the surface to specify the bond surface, and "Imperva Bond" bonding agent was applied to the specified surface, which in turn was subjected to visible light irradiation by "Shofu" GRIP LIGHT II (Shofu Inc.) for 10 seconds, so that the surface was photo-cured. Subsequently, a plastic mold with an inner diameter of 4 mm and a height of 2 mm was fixed to the surface and "LIGHT-FIL II", a light cure composite resin, was filled into the interior of the mold. The surface was subjected to visible light irradiation by "Shofu" GRIP LIGHT II via the mold for 30 seconds. After light curing, the mold was removed and a bond test specimen was prepared for each tooth surface treating agent. The bond test specimen was immersed in distilled water at 37° C. for 24 hours. Then, measurement for tensile bond strength was made by "Shimadzu" AUTOGRAPH AG-5000G at a crosshead speed of 1 mm/min.

For purposes of comparison, a bond test was also conducted for the case where the ingredients were phosphoric acid and water only. The results are shown in Table 4.

TABLE 4

| Ingredient & bond strength | Ex. 12 | Ex. 13 | Ex. 14 | Ex. 15 | Comp. Ex 8 |
|---|---|---|---|---|---|
| Phosphoric acid | 10 | 7 | 5 | 1 | 10 |
| TMBA | 3 | 3 | 3 | 3 | — |
| Water | 87 | 90 | 92 | 96 | 90 |
| Bond strength to dentin (kgf/cm$^2$) | 140.4 | 150.0 | 171.0 | 136.9 | 83.1 |

(Note) Ingredient proportions are shown in wt %.

In these examples, tensile bond tests were carried out using freshly extracted bovine teeth with pulp as a dento-clinical model for vital teeth (teeth with pulp). In Examples. 12 to 15, the compositions exhibited significantly high bond strength as compared with the composition of the conventional type used in Comparative Example 8. It had been reported that if the dentin of teeth with pulp was subjected to acid etching, the dentinal tubule would be open to allow dental fluid to well out, resulting in decreased bond strength. However, whereas in Comparative Example 8 in which acidic compound (phosphoric acid) was the only ingredient except water, there did occur a decrease in bond strength, the compositions in Examples 12 to 15 exhibited high bond strength by virtue of the polymerization catalyst (TMBA) present therein.

Examples 16 to 30

In each case, to a mixture of L-ascorbic acid (AA) and phosphoric acid (PA) in the proportions shown in Table 5 was added distilled water to a total of 100 % by weight, whereby a tooth surface treating agent was prepared. Shear bond tests to the teeth were carried out using the tooth surface treating agents shown in Table 5 in the same way as in Example 1, except that rubbing was effected in connection with the primer treatment of the dentin. The results are shown in Table 5.

TABLE 5

|  | Ingredient & Quantity | | Shear Bond strength (kgf/cm$^2$) | |
|---|---|---|---|---|
|  | AA | PA | Enamel | Dentin |
| Example 16 | 0.1 | 10 | 206.4 | 164.8 |
| Example 17 | 0.1 | 40 | 184.2 | 200.2 |
| Example 18 | 0.1 | 50 | 253.9 | 150.4 |
| Example 19 | 0.1 | 60 | 148.9 | 165.2 |
| Example 20 | 0.1 | 70 | 186.2 | 144.6 |
| Example 21 | 0.5 | 10 | 230.1 | 186.0 |
| Example 22 | 5 | 10 | 177.0 | 159.5 |
| Example 23 | 10 | 2 | 143.3 | 177.5 |
| Example 24 | 10 | 3 | 206.6 | 156.0 |
| Example 25 | 10 | 5 | 130.5 | 148.5 |
| Example 26 | 10 | 10 | 223.9 | 140.5 |
| Example 27 | 10 | 40 | 155.2 | 158.7 |
| Example 28 | 20 | 10 | 168.5 | 131.9 |
| Example 29 | 25 | 10 | 204.3 | 194.5 |
| Example 30 | 25 | 25 | 197.9 | 140.1 |

(Note) Ingredient proportions are shown in wt %.

Examples 31 to 37

In each case, to a mixture of polymerization catalyst and acidic compound in the proportions shown in Table 6 was added distilled water to a total of 100% by weight, whereby a tooth surface treating agent was prepared. Shear bond tests to the teeth were carried out in the same way as in Example 16 using the tooth surface treating agents shown in Table 6. The results are shown in Table 6.

TABLE 6

|  | Ingredient & Quantity | | | Shear Bond Strength (kgf/cm$^2$) | |
|---|---|---|---|---|---|
|  | Polymerization catalyst (wt %) | | Acidic compound (wt %) | Enamel | Dentin |
| Example 31 | CEBA | 0.1 | PA 10 | 175.6 | 152.4 |
| Example 32 | BBA | 0.3 | PA 10 | 271.1 | 263.2 |
| Example 33 | BPBA | 0.1 | PA 10 | 151.3 | 218.5 |
| Example 34 | AA | 0.5 | MA 35 | 155.6 | 209.4 |
| Example 35 | AA | 0.5 | CA 40 | 130.6 | 195.0 |
| Example 36 | AA | 0.1 | TA 40 | 210.7 | 155.2 |
| Example 37 | AA | 0.1 | TA 50 | 232.7 | 178.7 |

(Note) Ingredient proportions are shown in wt %.
CEBA: 1-cyclohexyl-5-ethylbarbituric acid
BBA: 5-butylbarbituric acid
BPBA: 1-benzyl-5-phenylbarbituric acid
AA: L-ascorbic acid
PA: Phosphoric acid; MA: maleic acid;
CA: citric acid; TA: Tartaric acid

Examples 38 to 46

In each case, to a mixture of polymerization catalyst and acidic compound in the proportions shown in Table 7 was added distilled water to a total of 100% by weight, whereby a tooth surface treating agent was prepared. Shear bond tests to the teeth were carried out in the same way as in Example 16 using the tooth surface treating agents shown in Table 7. The results are shown in Table 7.

TABLE 7

| Ingredient & bond strength | Example | | | | | |
|---|---|---|---|---|---|---|
|  | 38 | 39 | 40 | 41 | 42 | 43 |
| t-BPMA | 0.5 | — | — | 0.5 | — | — |
| SAPO | — | 3 | — | — | — | — |
| t-BHPO | — | — | 3 | — | 3 | 3 |
| TA | — | — | — | 45 | — | 30 |
| MA | — | — | — | — | 30 | 10 |
| PA | 10 | 10 | 10 | — | — | — |
| Bond strength (kg/cm$^2$) |  |  |  |  |  |  |
| to enamel | 262.3 | 225.7 | 233.6 | 267.1 | 181.1 | 257.5 |
| to dentin | 177.1 | 154.7 | 247.6 | 162.8 | 140.9 | 226.9 |

(Note) Ingredient proportions are shown in wt %.
t-BPMA: t-butylperoxymaleic acid;
SAPO: succinic acid peroxide;
t-BHPO: t-butyl hydroperoxide;
TA: tartaric acid; MA: maleic acid;
PA; phosphoric acid;
4-AET: 4-acryloxyethyltrimellitic acid;
4-AETA: 4-acryloxyethyltrimellitic acid anhydride;
MEPP: (2-methacryloxyethyl phenyl) phosphoric acid.

Examples 47 to 51

Two-liquid type tooth surface treating agents were prepared in such a way that A-C liquids comprised of acidic compounds and distilled water mixed in such varied proportions as shown in Table 8 were prepared on one hand and D-E liquids comprised of polymerization catalysts and distilled water mixed in such varied proportions as shown were prepared on the other hand. Bond tests were carried out using the tooth surface treating agents in the same way as in Example 16, except that tooth surfaces were treated according to the conditions shown in Table 9.

TABLE 8

|  | Ingredients & Quantity | | |
|---|---|---|---|
|  | Polymerization catalyst (wt %) | Acidic compound (wt %) | Distilled water (wt %) |
| A liquid | — | 10% PA | 90% |
| B liquid | — | 30% MA | 70% |
| C liquid | — | 30% TA | 70% |
| D liquid | 1% TMBA 4% p-TSNa | — | 95% |
| E liquid | 3% TMBA 3% BSNa | — | 94% |

(Note) Ingredient proportions are shown in wt %. PA: phosphoric acid; MA: maleic acid; TA: tartaric acid; TMBA: 1,3,5-trimethylbarbituric acid; p-TSNa: p-toluenesulfinic acid sodium salt; BSNa: benzenesulfinic acid sodium salt.

TABLE 9

|  | Tooth Surface Treating Method | Shear Bond strength (kgf/cm$^2$) | |
|---|---|---|---|
|  |  | Enamel | Dentin |
| Example 47 | Apply equal part mixture of A liquid + D liquid | 165.6 | 144.1 |
| Example 48 | Apply equal part mixture of B liquid + D liquid | 167.5 | 180.3 |
| Example 49 | Apply equal part mixture of C liquid + D liquid | 226.1 | 150.4 |
| Example 50 | Apply equal part mixture of A liquid + E liquid | 222.1 | 151.3 |
| Example 51 | Apply A liquid, then apply D liquid | 143.7 | 153.6 |

Example 52

Using a tooth surface treating agent prepared from a mixture of 10 wt % of phosphoric acid, 3 wt % of t-butyl hydroperoxide, and 87 wt % of distilled water, surface treatment and primer treatment were carried out with respect to the enamel and dentin. Dual-cure type resin cement "Imperva Dual" (Shofu Inc.) was then applied to the enamel and dentin according to the instruction manual, whereby bond test specimens were prepared. Shear bond tests were carried out with these specimens in the same way as in Example 16. The tests witnessed enamel bond strength of 179.1 kgf/cm$^2$ and dentin bond strength of 205.4 kgf/cm$^2$. For comparison purposes, bond tests were carried out without using the tooth surface treating agent, to find enamel bond strength of 35.4 kgf/cm$^2$, and dentin bond strength of 52.1 kgf/cm$^2$.

Example 53

A powder-form tooth surface treating agent was prepared from a mixture of 1 part by weight of t-butyl hydroperoxide, and 10 parts by weight of tartaric acid. Bond test was carried out in the same way as in Example 16, except that the tooth surface treating agent was substituted for the tooth surface treating agent used in Example 16.

Tooth surface treatment was effected in such a manner that 0.02 g of the tooth surface treating agent was placed on ground bovine teeth prepared in the same way as in Example 16 which was after-wash wet condition (its surface being wet with 0.02 g of water). The composition was gently stirred with a small brush to allow it to be dissolved. After lapse of 60 seconds, the tooth surface was washed with water and dried. After surface treatment, shear bond test was carried out in the same way as in Example 16. The bond test witnessed an enamel bond strength of 143.3 kgf/cm$^2$ and a dentin bond strength of 141.7 kgf/cm$^2$.

Example 54

Using a tooth surface treating agent prepared from a mixture of 0.5 wt % of camphorquinone, 2.0 wt % of 1, 3, 5-trimethylbarbituric acid, 10 wt % of phosphoric acid, and 77.5 wt % of distilled water, shear bond test with the teeth was made in the same way as in Example 16, except that the tooth surface treating agent was substituted for the tooth surface treating agent used in Example 16.

The bond test witnessed an enamel bond strength of 188.7 kgf/cm$^2$ and a dentin bond strength of 187.5 kgf/cm$^2$, both of substantially same order at a high level.

Example 55

Using a tooth surface treating agent prepared from a mixture of 3.0 wt % of 3, 5-trimethylbarbituric acid, 12.2 wt % of polyacrylic acid, and 84.8 wt % of distilled water, shear bond tests were carried out in the same way as in Example 16, except that the tooth surface treating agent was substituted for the tooth surface treating agent in Example 16. After surface treatment and primer treatment, the enamel and dentin were subjected to bond tests. In this conjunction, bond test specimens were prepared by using a light cure type glass ionomer cement "Vitrebond" (3M Co.) according to the teaching of the instruction manual for the cement.

The tests witnessed an enamel bond strength of 133.7 kgf/cm$^2$ and a dentin bond strength of 95.5 kgf/cm$^2$. For comparison purposes, bond tests were carried out without using the tooth surface treating agent to find an enamel bond strength of 96.3 kgf/cm$^2$ and a dentin bond strength of 41.0 kgf/cm$^2$. It can be noted from this comparison that the tooth surface treating agent exhibited a particularly high bond performance with the dentin, say, more than two times as high as that in the case where the tooth surface treating agent was not used. This proved that the tooth surface treating agent of the invention would exhibit high adhesion performance even for the purpose of effecting bond between light-cure type glass ionomer cement and teeth.

EFFECT OF THE INVENTION

The tooth surface treating agent of the present invention which comprises a polymerization catalyst and an acidic compound and is capable of enhancing tooth adhesion is very useful for clinical purposes in dentistry. Where it is necessary to adhere dental adhesive restorative materials, such as bonding agent, composite resin, resin cement, or light-cure glass ionomer cement; fissure sealants; or orthodontic adhesives, to enamel and dentin substrates by simultaneous treatment, the tooth surface treating agent exhibits excellent adhesion performance.

The present invention is intended mainly for use in the field of dentistry, but is also applicable to other fields, such as surgery, plastic surgery, and orthopedic surgery.

We claim:
1. A tooth surface treating agent, comprising:
   0.01 to 30% by weight of a polymerization catalyst selected from the group consisting of ascorbic acids, a barbituric acid derivative, an organic peroxide, sulfinic acids, salts thereof and photo polymerization catalysts and a mixture thereof,
   1 to 70% by weight of an acidic compound which is nonpolymerizable and selected from the group consisting of phosphoric acid, tartaric acid, maleic acid, citric acid, ferric chloride, and polyacrylic acid, or a mixture thereof, and
   10 to 98% by weight of water,
   the tooth surface treating agent not containing a monomer and being suitable for cleaning tooth surface.

2. A tooth surface treating agent as set forth in claim 1, which may contain a solvent such as ethyl alcohol or acetone.

3. A tooth surface treating agent as set forth in claim 1, which may contain an oxidation inhibitor and/or a viscosity modifier.

4. A tooth surface treating agent of claim 1, comprising:
   0.1 to 25% by weight of a polymerization catalyst,
   1 to 35% by weight of an acidic compound, and balance of water,
   on the basis of the total amount of the polymerization catalyst, acidic compound and water, and being suitable for cleaning tooth surface.

5. A tooth surface treating agent as set forth in claim 1, wherein the polymerization catalyst is selected from the group consisting of L-ascorbic acid, 1, 3, 5-trimethylbarbituric acid, 1-cyclohexyl-5-ethylbarbituric acid, 5-butylbarbituric acid, 1-benzyl-5-phenylbarbituric acid, 1-butylperoxy maleic acid, succinic acid peroxide, t-butyl hydroperoxide, benzenesulfinic acid sodium salt, p-toluenesulfinic acid sodium salt, and camphorquinone and mixtures thereof.

6. A tooth surface treating agent as set forth in claim 2, wherein the polymerization catalyst is selected from the group consisting of L-ascorbic acid, 1, 3, 5-trimethylbarbituric acid, 1-cyclohexyl-5-ethylbarbituric acid, 5-butylbarbituric acid, 1-benzyl-5-phenylbarbituric acid, 1-butylperoxy maleic acid, succinic acid peroxide, t-butyl hydroperoxide, benzenesulfinic acid sodium salt, p-toluenesulfinic acid sodium salt, and camphorquinone and mixtures thereof.

7. A tooth surface treating agent as set forth in claim 2, which may contain a solvent such as ethyl alcohol or acetone.

8. A tooth surface treating agent as set forth in claim 2, which may contain an oxidation inhibitor and/or a viscosity modifier.

9. A tooth surface treating agent as set forth in claim 1, wherein the polymerization catalyst comprises L-ascorbic acid, 1, 3, 5-trimethylbarbituric acid, 1-cyclohexyl-5-ethylbarbituric acid, 5-butylbarbituric acid, 1-benzyl-5-phenylbarbituric acid, 1-butylperoxy maleic acid, succinic acid peroxide, t-butyl hydroperoxide, benzenesulfinic acid sodium salt, p-toluenesulfinic acid sodium salt, and camphorquinone, or a mixture thereof.

10. A tooth surface treating agent as set forth in claim 1, which may contain a solvent such as ethyl alcohol or acetone.

11. A tooth surface treating agent as set forth in claim 1, which may contain an oxidation inhibitor and/or a viscosity modifier.

* * * * *